United States Patent [19]

Konz

[11] 4,302,238
[45] Nov. 24, 1981

[54] HERBICIDAL ISOXAZOLIDINE-3,5-DIONES

[75] Inventor: Marvin J. Konz, Lockport, N.Y.

[73] Assignee: FMC Corporation, Philadelphia, Pa.

[21] Appl. No.: 180,053

[22] Filed: Aug. 20, 1980

Related U.S. Application Data

[63] Continuation-in-part of Ser. No. 46,148, Jun. 6, 1979, abandoned.

[51] Int. Cl.³ .................... A01N 43/80; C07D 261/12
[52] U.S. Cl. .......................................... 71/88; 548/243
[58] Field of Search ............................ 548/243; 71/88

[56] References Cited

U.S. PATENT DOCUMENTS 3,007,936 11/1961 Matter et al. ...................... 548/243
3,264,317 8/1966 Stoffel ..................................... 71/88

OTHER PUBLICATIONS

Zinner, et al., "Arch. Pharm.," 299(6), 562–568, (1966).
Zinner et al., "Pharmazi," (1974), 29(1), 16–20.

Primary Examiner—Anton H. Sutto
Attorney, Agent, or Firm—Harrison H. Young, Jr.; H. Robinson Ertelt

[57] ABSTRACT

2-Substituted isoxazolidine-3,5-diones and isoxazolidine-3-one-5-thiones exhibit herbicidal activity, controlling effectively the growth of a wide spectrum of grassy and broad-leaved plant species. The preparation and herbicidal activity of the compounds is exemplified.

21 Claims, No Drawings

HERBICIDAL ISOXAZOLIDINE-3,5-DIONES

This is a continuation-in-part of copending application U.S. Ser. No. 046,148, filed June 6, 1979, now abandoned.

This invention describes novel herbicidal compounds, new herbicidal compositions, and new methods for preventing and destroying undesired plant growth by preemergence application of the new and useful herbicidal compositions to the locus where control is desired. Effective control of the growth of a variety of both grassy and broadleaved plant species is obtained. At levels of application which prevent growth of a variety of weeds the compounds of the invention show selectivity favorable to soybeans, sorghum, lima beans, and peanuts. The herbicidal compositions may be applied and utilized by commonly accepted methods.

Isoxazolidine-3,5-diones have been described in the literature, for example in U.S. Pat. No. 3,007,936 (Nov. 7, 1961), by Michel et al. in *Helv. Chim. Acta* 48(8), 1973-83 (1965), by Zinner et al. in *Arch. Pharm.* 299(6) 562-8 (1966), and by Zinner et al. in *Pharmazie* 1974, 29(1) 16-20. While these publications disclose methods of preparation for a variety of isoxazolidinediones and pharmaceutical activity for some members of the class, no reference has been found to herbicidal activity for any isoxazolidinedione.

The herbicidal compounds of this invention have the formula

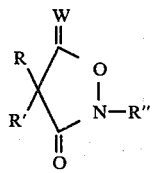

where
R and R' are the same or different and are hydrogen, lower alkyl (1 to 4 carbon atoms), phenyl, or benzyl, or taken together are an alkylene group of 2 or more carbon atoms, e.g., 2 to 5 carbon atoms;
R" is alkyl or alkenyl (each of two or more carbon atoms) or cycloalkyl or cycloalkenyl, each optionally substituted, e.g., with halogen, or is —CYY'—$X_m$—Z;
Y and Y' are the same or different and are hydrogen, halogen, or lower alkyl or phenyl, each optionally substituted, e.g., with halogen; X is an alkylene group of 1 to 4 carbon atoms; m is 0 or 1; and Z is hydrogen; a hydrocarbon group of 1 to 7 carbon atoms, optionally linked to X through oxygen, sulfur, or —NQ—, where Q is hydrogen, lower alkyl, or aryl; or a heterocyclic group of 3 to 6 members; and each Z other than hydrogen may be substituted with one or more groups independently selected from halogen, lower alkyl, lower alkoxy, methylenedioxy, amino, dimethylamino, trifluoromethyl, nitro, cyano, or carbalkoxy.

A representative class of compounds is that in which R" is —CHY—$X_m$—Z, where Z is aryl, e.g., phenyl, furyl, thienyl, pyridyl, or pyrimidyl, and has one or more substituents.

A preferred class of compounds is that in which R" is —CH$_2$—Z and Z is phenyl having one or two substituents independently selected from methyl, methylenedioxy, and halogen, e.g., chlorine, bromine, or fluorine.

Within this class particularly preferred are those compounds in which R and R' are each methyl and the phenyl group has a halogen substituent in the 2-position.

In general the compounds of the invention may be prepared by reacting a hydroxylamine, R"—NHOH, with a malonic acid chloride, RR'C(COCl)$_2$, in a solvent, such as a dry aromatic or aliphatic hydrocarbon or chlorinated hydrocarbon, and in the presence of an acid acceptor, e.g., pyridine or a tertiary amine such as triethylamine, at a temperature in the range of −80° to 50° C.

Preparation of the compounds of the invention and of intermediates from which they are prepared is exemplified below. In the descriptions which follow, all temperatures are in degrees centigrade, and reduced pressures are in millimeters of mercury, or if not otherwise specified, were obtained by means of a water aspirator.

EXAMPLE I

2-[(2-Chlorophenyl)methyl]-4,4-dimethylisoxazolidine-3,5-dione

Step A: Synthesis of 2-chlorobenzaldoxime

To a stirred solution of 56.2 grams (0.40 mole) of 2-chlorobenzaldehyde and 55.6 grams (0.80 mole) of hydroxylamine hydrochloride in 225 ml of ethanol and 111 ml of water was added in portions over a 15 minute period a solution of 24.0 grams (0.60 mole) of sodium hydroxide in 24 ml of water. The addition caused a solid precipitate to form. The reaction mixture was heated to boiling, and water was added until the solid dissolved. Additional water was added until the solution became cloudy. The reaction mixture was allowed to cool, and as it cooled a crystalline solid formed. The solid, collected by filtration, was dissolved in methylene chloride, and the methylene chloride solution was dried with sodium sulfate. The filtrate was concentrated under reduced pressure to remove ethanol, yielding additional solid, which was collected by filtration. This solid, too, was dissolved in methylene chloride, and the solution was dried with sodium sulfate. The two methylene chloride solutions were filtered from the sodium sulfate and the filtrates combined and concentrated under reduced pressure to give a residual solid. The solid was recrystallized from ethanol-water to give 48.3 grams of 2-chlorobenzaldoxime; mp 73.5°–75.5° C. The nmr and the ir spectra were consistent with the assigned structure.

Step B: Synthesis of N-(2-chlorophenylmethyl)hydroxylamine

A solution of 26.0 grams (0.7 mole) of 2-chlorobenzaldoxime and a trace of methyl orange indicator in 200 ml of methanol was stirred in a flask equipped with a drying tube and two dropping funnels. A solution of 13.2 grams (0.21 mole) of sodium cyanoborohydride in 70 ml of methanol and a solution of 190 ml of methanolic 2 N hydrochloric acid were both added dropwise with the rates of addition adjusted to keep the pH of the reaction mixture at about 3.0 as shown by the pink color of the indicator. The borohydride solution was added over a period of about thirty minutes: addition of the acid solution was complete after about four and one half hours. The reaction mixture was stirred at room temperature for about 16 hours and then concentrated under reduced pressure to a solid residue. The solid was slurried with 200 ml of water. The mixture was adjusted to pH 9 with aqueous 6 N potassium hydroxide and then extracted with one portion of 300 ml of chloroform. The organic layer was washed with an aqueous solution saturated with sodium chloride and then dried with sodium sulfate. The solution was filtered from the sodium sulfate, and the filtrate was concentrated under reduced pressure to give a residual solid. The solid was twice recrystallized from 15% ethyl acetate in hexane to give 13.7 grams of N-(2-chlorophenylmethyl)hydroxylamine; mp 73°–75.5° C. The nmr and the ir spectra were consistent with the assigned structure.

Calc'd for $C_7H_8ClNO$: C 53.35; H 5.11; N 8.89; Found: C 53.68; H 5.20; N 8.81.

Step C: Synthesis of 2-[(2-chlorophenyl)methyl]-4,4-dimethylisoxazolidine-3,5-dione To a stirred solution of 8.3 grams (0.053 mole) of N-(2-chlorophenylmethyl)hydroxylamine and 12.1 grams (0.12 mole) of triethylamine in 200 ml of dry toluene was added dropwise a solution of 9.0 grams (0.053 mole) of dimethylmalonyl chloride in 50 ml of dry toluene. The addition required approximately 30 minutes and caused a white precipitate to form. The reaction mixture was stirred at room temperature for about 16 hours. The white precipitate was collected by filtration and washed with toluene. The combined wash and filtrate was washed with two portions of water and one portion of an aqueous solution saturated with sodium chloride and then dried with sodium sulfate. The solution was filtered from the sodium sulfate, and the filtrate was concentrated under reduced pressure to a viscous liquid. The liquid was subjected to column chromatography on silica gel. Elution was accomplished with 15% ethyl acetate in hexane. The fractions showing product by thin layer chromatography were combined to give an oil, which was distilled under reduced pressure to give 4.0 grams of 2-[(2-chlorophenyl)methyl]-4,4-dimethylisoxazolidine-3,5-dione; bp 115° C./0.03 mm. The nmr and the ir spectra were consistent with the assigned structure.

Calc'd for $C_{12}H_{13}ClNO_3$: C 56.81; H 4.77; N 5.52; Found: C 57.06; H 4.75; N 5.80.

Following the same procedures as in Example I (Steps A and B), appropriately substituted benzaldehydes were converted to oximes, and thence to hydroxylamines, to obtain intermediates for further compounds. These intermediates, characterized by nmr and ir spectra and elemental analysis, included (D) N-(2,5-dichlorophenylmethyl)hydroxylamine (mp 91°–93° C.);
(E) N-(2,4-dichlorophenylmethyl)hydroxylamine (mp 69°–71° C.);
(F) N-(2-fluorophenylmethyl)hydroxylamine (mp 44.5°–45.5° C.);
(G) N-(2-bromophenylmethyl)hydroxylamine (mp 67°–68° C.); and
(H) N-[(6-chloro-1,3-benzenedioxol-5-yl)methyl]hydroxylamine (mp 84°–86.5° C.).

EXAMPLE II

2-[(2,5-Dichlorophenyl)methyl]-4,4-dimethylisoxazolidine-3,5-dione

To a stirred solution of 4.1 grams (0.024 mole) of dimethylmalonyl chloride and 3.8 grams (0.048 mole) of pyridine in 100 ml of dry toluene at 0° C., 4.7 grams (0.024 mole) of N-(2,5-dichlorophenylmethyl)hydroxylamine (Intermediate D) was added dropwise over 30 minutes, while the temperature was maintained at 0°±5° C. The reaction mixture was allowed to rise to ambient temperature and was stirred about 16 hours. A white solid was separated and washed with toluene. Filtrate and washings were combined, washed with water and saturated aqueous sodium chloride solution, and dried over sodium sulfate. Sodium sulfate was separated, and the liquid was concentrated under reduced pressure to a viscous liquid, and ultimately to a solid. Recrystallization from hexane-ethyl acetate yielded 2.7 grams of solid product; mp 78°–80° C. The nmr and ir spectra were consistent with the assigned structure.

Calc'd for $C_{12}H_{11}Cl_2NO_3$: C 50.02; H 3.85; N 4.86; Found: C 50.20; H 4.05; N 4.77.

EXAMPLE III

2-[(2,4-Dichlorophenyl)methyl]-4,4-dimethylisoxazolidine-3,5-dione

Seventy-five ml of methylene chloride and 9.6 ml (0.12 mole) of pyridine were placed in a flask under argon and cooled to 0° C. To this solution 8.4 grams (0.05 mole) dimethylmalonylchloride in 20 ml methylene chloride was added dropwise with stirring. This mixture was cooled to −70° C. and 9.6 g (0.05 mole) of N-(2,4-dichlorophenylmethyl)hydroxylamine (Intermediate E) was added in a single portion, and the temperature rose to 35° C. Stirring was continued for two hours at −10° C., and at ambient temperature for about 18 hours. The reaction mixture was washed with 2 N hydrochloric acid and saturated aqueous sodium chloride solution, and the methylene chloride layer was dried over sodium sulfate, which was removed by filtration. The filtrate was evaporated under reduced pressure and the resulting viscous liquid was subjected to column chromatography on silica gel. Elution was accomplished with 25% ethyl acetate in hexane. Cuts 3–11 were combined and solvent was removed under reduced pressure, yielding a light orange viscous liquid. This solidified as 6.5 grams of product (45% yield); mp 68°–69.5° C. The nmr and ir spectra were consistent with the assigned structure.

Calc'd for $C_{12}H_{11}Cl_2NO_3$: C 50.02; H 3.85; N 4.86; Found: C 49.90; H 3.75; N 4.78.

EXAMPLE IV

2-[(2-Fluorophenyl)methyl]-4,4-dimethylisoxazolidine-3,5-dione

The procedure of Example III was utilized with 10.2 ml (0.128 mole) pyridine, 10.2 grams (0.060 mole) dimethylmalonyl chloride and 120 ml methylene chloride in solution under argon at −72° C., to which 8.5 grams (0.060 mole) of N-(2-fluorophenylmethyl)hydroxylamine (Intermediate F) in 25 ml methylene chloride was added in a single portion, raising the temperature immediately to −25° C., and stirring was continued at 0° C. for two hours. Gas chromatography on a sample of the reaction mixture showed only one major peak. The reaction mixture was washed with 2 N hydrochloric acid and water, the methylene chloride layer was separated and dried over sodium sulfate, and after removal of sodium sulfate by filtration, the solvent was removed under reduced pressure, leaving 13.0 grams of a yellow viscous liquid (91% yield). The nmr and ir spectra were consistent with the assigned structure.

Calc'd for $C_{12}H_{12}FNO_3$: C 60.76; H 5.10; N 5.90; Found: C 60.67; H 5.27; N 5.71.

EXAMPLE V

2-[(2-Bromophenyl)methyl]-4,4-dimethylisoxazolidine-3,5-dione

The procedure of Example IV was followed, utilizing 7.0 grams (0.035 mole) of N-(2-bromophenylmethyl)hydroxylamine (Intermediate G). Product recovered consisted of 7.7 grams of a yellow viscous liquid, which solidified; mp 44.5°–45.5° C. The nmr and ir spectra were consistent with the assigned structure.

Calc'd for $C_{12}H_{12}BrNO_3$: C 48.34; H 4.06; N 4.70; Found: C 48.05; H 3.92; N 4.52.

EXAMPLE VI

2-[(6-Chloro-1,3-benzodioxol-5-yl)methyl]-4,4-dimethylisoxazolidine-3,5-dione The procedure of Example IV was followed, utilizing 7.0 grams (0.035 mole) of N-[(6-chloro-1,3-benzenediox-ol-5-yl)methyl]-hydroxylamine, except that an initial yellow solid product (9.4 grams; mp 82°–91° C.) was dissolved in methylene chloride and passed through a silica gel column. Fractions 3–10 were combined, solvent was removed under reduced pressure, and 5.2 grams of white solid were obtained; mp 93.5°–95° C. The nmr and ir spectra were consistent with the assigned structure.

Calc'd for $C_{13}H_{12}ClNO_5$: C 52.45; H 4.06; N 4.71; Found: C 52.29; H 4.16; N 4.70.

EXAMPLE VII

2-[(2-Chlorophenyl)methyl]-4-ethyl-4-methylisoxazolidine-3,5-dione

Step A: Synthesis of diethyl 2-ethyl-2-methylmalonate

To a stirred solution of 40.0 grams (0.23 mole) of diethyl 2-methylmalonate and 50.2 grams (0.46 mole) of bromoethane in 200 ml of dry dimethylformamide was added 79.5 grams (0.58 mole) of potassium carbonate. The resulting mixture was stirred at ambient temperature for 16 hours. A sample of the reaction mixture was subjected to analysis by vapor phase chromatography (VPC), which indicated the reaction had not gone to completion. An additional 50.2 grams of bromoethane was added and the reaction mixture stirred at ambient temperature for three days. VPC analysis indicated the reaction to be 80.9% complete. The reaction mixture was heated to 50° C. where it was stirred for one day. VPC analysis at this time indicated the reaction to be 88.8% complete. The reaction mixture was filtered and the filter cake washed with 200 ml of methylene chloride. The filtrate was diluted with 500 ml of methylene chloride and the combination washed with three portions of 500 ml each of water. The organic layer was dried with magnesium sulfate and filtered. The filtrate was concentrated under reduced pressure to a residual oil. The oil was distilled under reduced pressure to give 40.9 grams of diethyl 2-ethyl-2-methylmalonate; bp 109°–112° C./25 mm. The nmr and ir spectra were consistent with the assigned structure.

Analysis calc'd for $C_{10}H_{18}O_4$: C 59.38; H 8.97; Found: C 58.67; H 8.86.

Step B: Synthesis of 2-ethyl-2-methylmalonic acid

To a stirred solution of 38.5 grams (0.19 mole) of diethyl 2-ethyl-2-methylmalonate in 175 ml of tetrahydrofuran was added dropwise a solution of 76.0 grams (1.90 moles) of sodium hydroxide in 70 ml of water. The addition required 20 minutes and the temperature of the reaction mixture was maintained between 27°–31° C. Upon completion of addition, the reaction mixture was heated under reflux for 16 hours. The reaction mixture was diluted with 500 ml of water and washed with 200 ml of diethyl ether. The aqueous layer was cooled in an ice bath and acidified with concentrated hydrochloric acid to a pH of 1–2. The mixture was saturated with sodium chloride and extracted with six portions of 150 ml each of methylene chloride. The combined extracts were dried with magnesium sulfate and filtered. The filtrate was concentrated under reduced pressure to give 6.1 grams of solid; mp 119°–123° C. Additional sodium chloride was added to the original aqueous layer and the mixture extracted with ten portions of 150 ml each of diethyl ether. The combined extracts were dried with magnesium sulfate and filtered. The filtrate was concentrated under reduced pressure to give 9.1 grams of solid; mp 119°–123° C. The solids were combined to give 15.2 grams of 2-ethyl-2-methylmalonic acid. A small sample was recrystallized from hexane/ethyl acetate to raise the mp to 122°–123° C. The nmr and the ir spectra were consistent with the assigned structure.

Analysis calc'd for $C_6H_{10}O_4$: C 49.31; H 6.90; Found: C 49.21; H 7.07.

Step C: Synthesis of 2-ethyl-2-methylmalonyl dichloride

Under an argon atmosphere, 14.0 grams (0.096 mole) of 2-ethyl-2-methylmalonic acid were added to 75 ml of thionyl chloride. The stirred solution was heated under reflux for two hours, then concentrated under reduced pressure to give 16.7 grams of 2-ethyl-2-methylmalonyl dichloride as an oil. The ir spectrum was consistent with the assigned structure.

Step D: Synthesis of 2-[(2-chlorophenyl)methyl]-4-ethyl-4-methylisoxazolidine-3,5-dione This compound was prepared in the manner of Example IV, using 8.2 grams (0.045 mole) of 2-ethyl-2-methylmalonyl dichloride, 7.1 grams (0.045 mole) of N-(2-chlorophenylmethyl)hydroxylamine and 16 ml of pyridine in 184 ml of methylene chloride. After purification on a silica gel column, 8.2 grams of 2-[(2-chlorophenyl)methyl]-4-ethyl-4-methylisoxazolidine-3,5-dione were obtained as an oil. The nmr and the ir spectra were consistent with the assigned structure.

Analysis calc'd for $C_{13}H_{14}ClNO_3$: C 58.32; H 5.27; N 5.23; Found: C 58.08; H 5.17; N 5.02.

EXAMPLE VIII

2-[(2-Chlorophenyl)methyl]-4,4-dimethylisoxazolidine-3-one-5-thione

Step A: Synthesis of dimethylketene

Under an argon atmosphere, a stirred mixture of 13.3 grams (0.20 mole) of zinc in 100 ml of ethyl acetate was heated to a gentle reflux. To this was added dropwise 37.0 grams (0.16 mole) of 2-bromo-2-methylpropanoyl bromide. The product dimethylketene was collected by co-distillation with the ethyl acetate solvent. A total of 70.0 grams of solution was collected which was 8% (5.6 grams) dimethylketene.

Step B: Synthesis of dimethylthiomalonyl dichloride

To a stirred solution of 7.2 ml (9.2 grams, 0.08 mole; 85% in carbon tetrachloride) of thiophosgene in 50 ml of carbon tetrachloride under an argon atmosphere was added dropwise 70.0 grams of an ethyl acetate solution containing 5.6 grams (0.08 mole) of dimethylketene. The addition required five minutes during which time the reaction mixture temperature rose from 25° C. to 32° C. Upon completion of addition the reaction mixture was stirred at ambient temperature for 16 hours. The reaction mixture was concentrated under reduced pressure to a semi-solid residue. The residue was slurried in petroleum ether and a solid collected by filtration. The solid, mp 112°–114° C., was the dimethylketene dimer. The filtrate was concentrated under reduced pressure to a residual oil. The oil was distilled under reduced pressure to give 2.2 grams of dimethylthiomalonyl dichloride; bp 62°–67° C./8–8.5mm. The nmr spectrum was consistent with the assigned structure.

Calc'd for $C_5H_6Cl_2OS$: C 32.44; H 3.27; Cl 38.31; S 17.32; Found: C 31.74; H 3.39; Cl 36.76; S 16.03.

Step C: Synthesis of 2-[(2-chlorophenyl)methyl]-4,4-dimethylisoxazolidine-3-one-5-thione A stirred solution of 9.5 grams (0.12 mole) of pyridine in 170 ml of methylene chloride under an argon atmosphere was cooled to $-10°$ C. and a solution of 11.1 grams (0.06 mole) of dimethylthiomalonyl chloride in 30 ml of methylene chloride was added slowly. The reaction mixture was cooled to $-40°$ C. and 9.5 grams (0.06 mole) of N-(2-chlorophenylmethyl)hydroxylamine was added in one portion. The addition caused the reaction mixture temperature to quickly rise to $-20°$ C. The reaction mixture was stirred at $-20°$ C. for one hour, then was diluted with 150 ml of methylene chloride. The solution was washed with 100 ml of water, two portions of 75 ml each of aqueous 2 N hydrochloric acid, and finally, 50 ml of water. The organic layer was dried with magnesium sulfate and filtered. The filtrate was concentrated under reduced pressure to a residual oil. The oil was purified by column chromatography using 450 grams of silica gel. Elution was accomplished with chloroform. Early fractions from the chromatography yielded 5.3 grams of 2-[(2-chlorophenyl)methyl]-4,4-dimethylisoxazolidine-5-one-3-thione; mp 51°–53° C. Later fractions were combined to give 2.2 grams of 2-[(2-chlorophenyl)methyl]-4,4-dimethylisoxazolidine-3-one-5-thione as an oil. The nmr and the ir spectra were consistent with the proposed structure.

Calc'd for $C_{12}H_{12}ClNO_2S$: C 53.43; H 4.48; N 5.19; S 11.88; Found: C 53.10; H 4.64; N 5.15; S 12.10.

The isoxazolidine-5-one-3-thione was herbicidally inactive, and the isoxazolidine-3-one-5-thione is seen in Table 2 to be very active.

The test species used in demonstrating the herbicidal activity of compounds of this invention were lima bean (*Phaseolus limensis* Macfad), wild oats (*Avena fatua* L.), barnyardgrass (*Echinochloa crusgalli* L.), green foxtail (*Setaria viridis* L.), velvetleaf (*Abutilon theophrasti* Medic), tomato (*Lycopersicon esculentum* L.), soybean (*Glycine max*), cotton (*Gossypium hirsutum*), wheat (*Triticum aestivum*), sweet corn (*Zea mays* L.), sorghum (*Sorghum vulgare*), common ragweed (*Ambrosia artemisiifolia* L.), field bindweed (*Convolvulus arvenis* L.), jimsonweed (*Datura stramonium* L.), cocklebur (*Xanthium pensylvanicum* Wallr.), pigweed (*Amaranthus retroflexus* L.), tall morningglory (*Ipomoea purpurea*), mustard (*Brassica juncea* L. Cosson), johnsongrass (*Sorghum halepense* (L.)), bermudagrass (*Cynodon dactylon* (L.)), crabgrass (*Digitaria sanguinalis* L. Scop.), purslane (*Portulaca oleracea* L.), blue panicum (*Panicum antidotale*), wild buckwheat (*Polygonum convolvulus* L.), peanuts (*Arachis hypogaea*), sugarbeet (*Beta vulgaris*), blackgrass (*Alopercurus myosurides* (L.)), goosegrass (*Elusine indica* (L.)), lambsquarter (*Chenopodium album* L.), purple nutsedge (*Cyperus rotundus* L.), yellow nutsedge (*Cyperus esculentus*), sesbania (*Sesbania exaltata*).

For the preemergence test, seeds of the test species were planted in $15 \times 20 \times 8$ cm flats containing approximately a 5 cm depth of sandy loam soil. Prior to seeding the rows were marked by pressing a wooden template onto the soil surface. After the seeds were sown, a thin layer of soil (approximately 1.0 cm) was applied to the surface of the flat. The spray solutions containing the herbicide of the invention were then applied directly to the soil as aqueous solutions at rates equivalent to 4.00 kg active ingredient per hectare and four submultiples thereof (i.e., 2.00 kg/ha, 1.00 kg/ha, 0.50 kg/ha, and 0.25 kg/ha) and at a volume equivalent to 750 liters per hectare.

Purple nutsedge plants for the test were grown in pots containing viable purple nutsedge tubers planted at a depth of 2.5 cm. These plantings were also treated with the herbicide of the invention.

The test plants were maintained in a greenhouse and watered regularly on the soil surface for a period of nineteen days, at which time phytotoxicity was observed and recorded. Results are shown in Table 1 and 2.

The characteristic phytotoxic effects of the compounds of the invention are chlorosis and stunting. Under the conditions of the evaluation reported in Table 1 a wide variety of both grassy and broadleaved weeds were controlled at a rate of 1.0 kg/ha, a rate at which crop survival was good for sorghum, peanuts, and lima beans. For soybeans crop survival was good at a rate of 2.0 kg/ha, a treatment rate which gave excellent control of most of the weed species tested.

For herbicidal application the active isoxazolidine-3,5-diones of this invention will not ordinarily be applied in undiluted form, but will be diluted or extended with an agriculturally acceptable, relatively inert material, here called a carrier, which may be liquid or solid. Thus the compounds of this invention may be utilized in diverse formulations prepared from agricultural adjuvants and agricultural carriers to give the herbicidal compositions contemplated herein. The herbicidal compositions contain between about 0.01% and 95% active isoxazolidine-3,5-dione together with between about 4% and 98.5% agriculturally acceptable carrier and between about 1% and 15% surface active agent by weight. As is well-known in the art, the formulation and mode of application of a toxicant may affect the activity of the material in a given application. Thus, a compound of this invention may be formulated as an emulsifiable concentrate, as a granule of relatively large particle size, as a wettable powder, as a solution, or as any of several other known types of formulations, depending on the desired mode of application.

Emulsifiable concentrates are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other non-volatile organic solvents. For example, a useful emulsifiable concentrate formulation, designated "4EC" because it contains four pounds of active ingredient per gallon of concentrate (0.479 kg/liter), contains 53.01 parts of 2-[(2-chlorophenyl)methyl]-4,4-dimethylisoxazolidine-3,5-dione, 6.0 parts of a blend of alkylnaphthalenesulfonate and polyoxyethylene ethers as emulsifiers, 1.0 part of epoxidized soybean oil as stabilizer, and as solvent 39.99 parts of petroleum distillate having a high flash-point.

Granular formulations are particularly useful for aerial distribution. Useful granular formulations may be of several types. Impregnated granules are those wherein the active ingredient is applied to large particles of an absorbent carrier, such as an attapulgite or kaolin clay, corncobs, expanded mica, etc., normally in the form of a solution in a solvent. Surface-coated granules may be produced by spraying the molten active ingredient onto the surface of a generally nonabsorbent particle or by spraying on a solution of active ingredient in a solvent. The core may be watersoluble such as a prilled fertilizer, or insoluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for preemergence herbicides, are in the form of finely divided particles which disperse readily in water or other dispersants. The wettable powder is ultimately applied to the soil as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbability of the active ingredient and on the absorbency of the carrier, and usually also contain a small amount of a wetting, dispersing or emulsifying agent to facilitate dispersion.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface active agents, many of which are available in commerce. The surface-active agent, when used, normally comprises from 1% to 15% by weight of the herbicidal composition.

These formulations may be applied without further dilution or as dilute solutions, emulsions or suspensions in water or other suitable diluent. The compositions may be applied to the area wherein control is desired by spraying onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compound of this invention may be formulated and/or applied with insecticides, fungicides, nematicides, plant-growth regulators, fertilizers, and other agricultural chemicals. In applying the active compounds of this invention, whether formulated alone or with other agricultural chemicals, an effective amount and concentration of isoxazolidine-3,5-dione are of course employed. The amount constituting an effective amount is variable, depending on a number of factors such as the type of soil, the expected pattern of rainfall or irrigation, the plant species to be controlled, and the crop, if any, to be grown. Generally, a uniform application of between 0.1 and 9 kilograms per hectare will be employed, for example, 0.28 to 4.48 kilograms per hectare.

It is apparent that various modifications may be made in the formulation and application of the novel compounds of this invention, without departing from the inventive concept herein, as defined in the following claims.

TABLE 1

Preemergence Herbicidal Activity of 2-[(2-Chlorophenyl)Methyl]-4,4-Dimethylisoxazolidine-3,5-dione (Compound of Example 1)

| Plant Species | Rate of Application (kilograms/hectare) | | | | | | | | | | | |
|---|---|---|---|---|---|---|---|---|---|---|---|---|
| | 0.5 | | | 1.0 | | | 2.0 | | | 4.0 | | |
| | V | K | F | V | K | F | V | K | F | V | K | F |
| Lima Bean | 4 | 0 | 9 | 4 | 0 | 9 | 3 | 0 | 9 | 2 | 80 | 9 |
| Wild Oat | 4 | 0 | 9 | 3 | 20 | 9 | 3 | 95 | 9 | 2 | 95 | 9 |
| Barnyardgrass | 4 | 20 | 9 | 0 | 100 | 0 | 0 | 100 | 0 | 0 | 100 | 0 |
| Green Foxtail | 4 | 0 | 9 | 4 | 10 | 9 | 3 | 95 | 9 | 0 | 100 | 0 |
| Velvetleaf | 3 | 20 | 9 | 2 | 90 | 9 | 2 | 50 | 2 | 2 | 95 | 9 |
| Tomato | 4 | 10 | 9 | 3 | 20 | 9 | 3 | 40 | 9 | 1 | 80 | 9 |
| Soybean | 5 | 0 | 0 | 4 | 0 | 9 | 4 | 0 | 9 | 4 | 0 | 2 |
| Cotton | 3 | 0 | 2 | 0 | 100 | 0 | 0 | 100 | 0 | 0 | 100 | 0 |
| Wheat | 4 | 10 | 9 | 3 | 90 | 9 | 3 | 80 | 9 | 0 | 100 | 0 |
| Corn | 3 | 30 | 9 | 0 | 100 | 0 | 0 | 100 | 0 | 0 | 100 | 0 |
| Sorghum | 4 | 0 | 9 | 4 | 0 | 9 | 3 | 40 | 9 | 0 | 100 | 0 |
| Ragweed | 4 | 20 | 9 | 3 | 90 | 9 | 2 | 80 | 9 | 0 | 100 | 0 |
| Bindweed | 4 | 10 | 9 | 4 | 10 | 9 | 3 | 60 | 9 | 3 | 30 | 9 |
| Jimsonweed | 3 | 0 | 9 | 2 | 20 | 9 | 2 | 20 | 9 | 1 | 70 | 9 |
| Cocklebur | 4 | 40 | 9 | 3 | 40 | 9 | 1 | 80 | 9 | 0 | 100 | 0 |
| Pigweed | 3 | 90 | 2 | 0 | 100 | 0 | 0 | 100 | 0 | 0 | 100 | 0 |
| Morningglory | 4 | 0 | 9 | 4 | 0 | 9 | 3 | 50 | 9 | 1 | 80 | 9 |
| Wild Mustard | 0 | 100 | 0 | 0 | 100 | 0 | 0 | 100 | 0 | 0 | 100 | 0 |
| Johnsongrass | 4 | 10 | 9 | 3 | 30 | 9 | 3 | 95 | 9 | 0 | 100 | 0 |
| Bermudagrass | 3 | 50 | 9 | 3 | 70 | 9 | 2 | 90 | 9 | 0 | 100 | 0 |
| Crabgrass | 2 | 95 | 9 | 0 | 100 | 0 | 0 | 100 | 0 | 0 | 100 | 0 |
| Purslane | 0 | 100 | 0 | 0 | 100 | 0 | 0 | 100 | 0 | 0 | 100 | 0 |

TABLE 1-continued

Preemergence Herbicidal Activity of 2-[(2-Chlorophenyl)Methyl]-4,4-Dimethylisoxazolidine-3,5-dione (Compound of Example 1)

| | Rate of Application (kilograms/hectare) | | | | | | | | | | | |
|---|---|---|---|---|---|---|---|---|---|---|---|---|
| | 0.5 | | | 1.0 | | | 2.0 | | | 4.0 | | |
| Plant Species | V | K | F | V | K | F | V | K | F | V | K | F |
| Blue Panicum | 4 | 30 | 9 | 3 | 90 | 9 | 2 | 95 | 9 | 0 | 100 | 0 |
| Wild Buckwheat | 4 | 0 | 9 | 4 | 20 | 9 | 3 | 30 | 9 | 2 | 20 | 9 |
| Peanut | 4 | 0 | 9 | 4 | 0 | 9 | 3 | 0 | 9 | 2 | 20 | 9 |
| Sugarbeet | 3 | 40 | 9 | 3 | 70 | 9 | 0 | 100 | 0 | 2 | 90 | 9 |
| Blackgrass | 4 | 0 | 9 | 4 | 0 | 9 | 3 | 60 | 9 | 3 | 70 | 9 |
| Goosegrass | 3 | 20 | 9 | 3 | 30 | 9 | 2 | 95 | 9 | 0 | 100 | 0 |
| Lambsquarter | 4 | 30 | 9 | 3 | 80 | 9 | 3 | 95 | 2 | 0 | 100 | 0 |
| Purple Nutsedge | | — | | | — | | 4 | 0 | 9 | 3 | 80 | 9 |

V = Vigor:
5 = Plants normal
4 = Slight injury; plants will or have already recovered.
3 = Moderate injury; plants expected to recover.
2 = Moderate to severe injury; plants are not expected to recover.
1 = Severe injury; plants will not recover.
0 = Dead plants.
K = Percent kill
F = Footnote designation:
1 = Necrosis
2 = Stunted
3 = Desiccation
4 = Axilary Growth Stimulation
5 = Nastic Responses
6 = Necrotic Spots
7 = Growth Stimulation
8 = Defoliant
9 = Chlorosis
10 = Intumescence
11 = Suspected germination failure
12 = Stand may have been affected by non-chemical factors.

TABLE 2

Preemergence Herbicidal Activity of Isoxazolidine-3,5-Diones and -3-One-5-Thione

| Compound | Rate of Application (kilograms/hectare) | | | | | | | | | | | |
|---|---|---|---|---|---|---|---|---|---|---|---|---|
| of Example | 0.5 | | | 1.0 | | | 2.0 | | | 4.0 | | |
| Plant Species | V | K | F | V | K | F | V | K | F | V | K | F |
| II | | | | | | | | | | | | |
| Lima Bean | 5 | 0 | 0 | 4 | 0 | 9 | 3 | 0 | 2 | 3 | 20 | 2 |
| Wild Oat | 4 | 0 | 9 | 4 | 0 | 9 | 4 | 0 | 9 | 4 | 0 | 9 |
| Barnyardgrass | 4 | 0 | 9 | 3 | 70 | 9 | 0 | 100 | 0 | 0 | 100 | 0 |
| Green Foxtail | 4 | 0 | 9 | 4 | 0 | 9 | 4 | 10 | 9 | 4 | 40 | 2 |
| Velvetleaf | 4 | 30 | 9 | 4 | 30 | 9 | 4 | 60 | 2 | 3 | 90 | 9 |
| Tomato | 5 | 0 | 0 | 5 | 0 | 0 | 4 | 0 | 9 | 4 | 0 | 9 |
| Field Bindweed | 4 | 30 | 9 | 4 | 30 | 9 | 0 | 100 | 0 | 3 | 90 | 2 |
| Soybean | 5 | 0 | 0 | 5 | 0 | 0 | 4 | 30 | 2 | 3 | 30 | 2 |
| Sorghum | 4 | 0 | 9 | 4 | 0 | 9 | 4 | 0 | 9 | 3 | 10 | 9 |
| Wild Mustard | 3 | 80 | 9 | 2 | 90 | 9 | 0 | 100 | 0 | 0 | 100 | 0 |
| Johnsongrass | 5 | 0 | 0 | 4 | 0 | 9 | 4 | 0 | 9 | 3 | 40 | 9 |
| Cocklebur | 5 | 0 | 0 | 5 | 0 | 0 | 4 | 0 | 2 | 4 | 0 | 9 |
| Morningglory | 4 | 0 | 9 | 4 | 0 | 9 | 4 | 0 | 9 | 3 | 20 | 9 |
| Purple Nutsedge | | — | | | — | | | — | | 4 | 0 | 1 |
| III | | | | | | | | | | | | |
| Lima Bean | 5 | 0 | 0 | 5 | 0 | 0 | 5 | 0 | 0 | 5 | 0 | 0 |
| Wild Oat | 4 | 0 | 0 | 4 | 10 | 2 | 4 | 10 | 9 | 3 | 50 | 9 |
| Barnyardgrass | 4 | 0 | 0 | 3 | 80 | 2 | 0 | 100 | 0 | 0 | 100 | 0 |
| Green Foxtail | 4 | 0 | 0 | 4 | 0 | 2 | 4 | 30 | 2 | 3 | 95 | 9 |
| Velvetleaf | 4 | 0 | 2 | 4 | 20 | 9 | 3 | 50 | 2 | 3 | 0 | 9 |
| Tomato | 4 | 20 | 9 | 4 | 20 | 9 | 3 | 0 | 9 | 3 | 50 | 9 |
| Field Bindweed | 4 | 30 | 2 | 4 | 0 | 2 | 2 | 90 | 2 | 0 | 100 | 0 |
| Soybean | 5 | 0 | 0 | 5 | 0 | 0 | 5 | 0 | 0 | 5 | 0 | 0 |
| Sorghum | 4 | 0 | 9 | 4 | 0 | 9 | 4 | 10 | 9 | 4 | 10 | 9 |
| Wild Mustard | 4 | 80 | 9 | 3 | 80 | 2 | 3 | 50 | 2 | 2 | 80 | 2 |
| Johnsongrass | 4 | 0 | 9 | 4 | 0 | 2 | 4 | 0 | 9 | 4 | 20 | 9 |
| Cocklebur | 5 | 0 | 0 | 5 | 0 | 0 | 4 | 0 | 9 | 4 | 0 | 9 |
| Morningglory | 4 | 0 | 9 | 4 | 0 | 9 | 4 | 20 | 9 | 3 | 30 | 9 |
| Purple Nutsedge | | — | | | — | | 5 | 0 | 0 | 4 | 0 | 9 |
| IV | | | | | | | | | | | | |
| Lima Bean | 5 | 0 | 0 | 5 | 0 | 0 | 4 | 0 | 2 | 4 | 0 | 9 |
| Wild Oat | 5 | 0 | 0 | 5 | 0 | 0 | 5 | 0 | 0 | 4 | 0 | 9 |
| Barnyardgrass | 5 | 0 | 0 | 5 | 0 | 0 | 4 | 0 | 9 | 4 | 60 | 9 |
| Green Foxtail | 5 | 0 | 0 | 5 | 0 | 0 | 4 | 40 | 0 | 4 | 20 | 9 |
| Velvetleaf | 4 | 0 | 9 | 4 | 0 | 9 | 4 | 0 | 9 | 3 | 0 | 9 |
| Tomato | 5 | 0 | 0 | 5 | 0 | 0 | 5 | 0 | 0 | 5 | 0 | 0 |
| Field Bindweed | 5 | 0 | 0 | 5 | 0 | 0 | 4 | 0 | 2 | 0 | 100 | 9 |
| Soybean | 5 | 0 | 0 | 5 | 0 | 0 | 5 | 0 | 0 | 5 | 0 | 0 |

TABLE 2-continued
Preemergence Herbicidal Activity of Isoxazolidine-3,5-Diones and -3-One-5-Thione

| Compound of Example Plant Species | Rate of Application (kilograms/hectare) | | | | | | | | | | |
|---|---|---|---|---|---|---|---|---|---|---|---|
| | 0.5 | | | 1.0 | | | 2.0 | | | 4.0 | |
| | V | K | F | V | K | F | V | K | F | V | K | F |
| Sorghum | 5 | 0 | 0 | 5 | 0 | 0 | 4 | 0 | 9 | 4 | 0 | 9 |
| Wild Mustard | 4 | 0 | 9 | 4 | 0 | 9 | 3 | 0 | 9 | 3 | 80 | 2 |
| Johnsongrass | 5 | 0 | 0 | 5 | 0 | 0 | 5 | 0 | 0 | 4 | 0 | 9 |
| Cocklebur | 5 | 0 | 0 | 5 | 0 | 0 | 5 | 0 | 0 | 4 | 0 | 9 |
| Morningglory | 5 | 0 | 0 | 5 | 0 | 0 | 4 | 0 | 9 | 4 | 0 | 9 |
| Purple Nutsedge | — | | | — | | | 5 | 0 | 0 | 5 | 0 | 0 |
| V | | | | | | | | | | | | |
| Lima Bean | 5 | 0 | 0 | 4 | 0 | 2 | 3 | 20 | 2 | 4 | 80 | 2 |
| Wild Oat | 4 | 0 | 9 | 4 | 0 | 9 | 4 | 0 | 9 | 4 | 10 | 9 |
| Barnyardgrass | 4 | 0 | 2 | 4 | 20 | 2 | 3 | 90 | 9 | 3 | 90 | 9 |
| Green Foxtail | 5 | 0 | 0 | 4 | 0 | 9 | 4 | 0 | 9 | 4 | 0 | 9 |
| Velvetleaf | 4 | 0 | 9 | 3 | 0 | 9 | 3 | 20 | 9 | 3 | 0 | 9 |
| Tomato | 4 | 0 | 9 | 4 | 0 | 9 | 4 | 0 | 9 | 3 | 0 | 9 |
| Field Bindweed | 5 | 0 | 0 | 4 | 30 | 2 | 4 | 0 | 2 | 4 | 0 | 2 |
| Soybean | 5 | 0 | 0 | 5 | 0 | 0 | 4 | 0 | 9 | 4 | 0 | 9 |
| Sorghum | 4 | 0 | 9 | 4 | 0 | 9 | 4 | 0 | 9 | 4 | 0 | 9 |
| Wild Mustard | 3 | 0 | 9 | 3 | 0 | 9 | 3 | 0 | 9 | 0 | 100 | 0 |
| Johnsongrass | 4 | 0 | 9 | 4 | 0 | 9 | 3 | 0 | 2 | 4 | 0 | 9 |
| Cocklebur | 5 | 0 | 0 | 4 | 0 | 9 | 4 | 0 | 9 | 3 | 0 | 9 |
| Morningglory | 4 | 0 | 9 | 4 | 0 | 9 | 4 | 0 | 9 | 3 | 50 | 2 |
| Purple Nutsedge | — | | | — | | | 5 | 0 | 0 | 5 | 0 | 0 |
| VI | | | | | | | | | | | | |
| Lima Bean | 5 | 0 | 0 | 5 | 0 | 0 | 4 | 0 | 4 | 3 | 0 | 4 |
| Wild Oat | 5 | 0 | 0 | 5 | 0 | 0 | 5 | 0 | 0 | 5 | 0 | 0 |
| Barnyardgrass | 4 | 30 | 0 | 4 | 70 | 9 | 3 | 90 | 9 | 3 | 90 | 9 |
| Green Foxtail | 5 | 0 | 0 | 5 | 0 | 0 | 4 | 0 | 9 | 4 | 0 | 9 |
| Velvetleaf | 5 | 0 | 0 | 5 | 0 | 0 | 4 | 0 | 9 | 5 | 0 | 0 |
| Tomato | 5 | 0 | 0 | 5 | 0 | 0 | 5 | 0 | 0 | 4 | 0 | 9 |
| Field Bindweed | 4 | 0 | 9 | 5 | 0 | 0 | 4 | 0 | 9 | 4 | 0 | 9 |
| Soybean | 5 | 0 | 0 | 5 | 0 | 0 | 5 | 0 | 0 | 5 | 0 | 0 |
| Sorghum | 5 | 0 | 0 | 5 | 0 | 0 | 5 | 0 | 0 | 5 | 0 | 0 |
| Wild Mustard | 5 | 0 | 0 | 4 | 0 | 9 | 3 | 0 | 9 | 3 | 80 | 9 |
| Johnsongrass | 5 | 0 | 0 | 5 | 0 | 0 | 5 | 0 | 0 | 5 | 0 | 0 |
| Cocklebur | 5 | 0 | 0 | 5 | 0 | 0 | 4 | 0 | 9 | 3 | 60 | 9 |
| Morningglory | 5 | 0 | 0 | 4 | 0 | 9 | 5 | 0 | 0 | 5 | 0 | 0 |
| Purple Nutsedge | — | | | — | | | — | | | 4 | 0 | 9 |
| VII | | | | | | | | | | | | |
| Lima Bean | 5 | 0 | 0 | 5 | 0 | 0 | 5 | 0 | 0 | 4 | 0 | 9 |
| Wild Oat | 5 | 0 | 0 | 5 | 0 | 0 | 4 | 0 | 9 | 4 | 0 | 9 |
| Barnyardgrass | 5 | 0 | 0 | 5 | 0 | 0 | 4 | 0 | 9 | 3 | 90 | 9 |
| Green Foxtail | 5 | 0 | 0 | 5 | 0 | 0 | 5 | 0 | 0 | 4 | 0 | 9 |
| Velvetleaf | 5 | 0 | 0 | 5 | 0 | 0 | 4 | 0 | 9 | 4 | 0 | 9 |
| Tomato | 5 | 0 | 0 | 5 | 0 | 0 | 5 | 0 | 0 | 5 | 0 | 0 |
| Field Bindweed | 5 | 0 | 0 | 5 | 0 | 0 | 5 | 0 | 0 | 5 | 0 | 0 |
| Soybean | 5 | 0 | 0 | 5 | 0 | 0 | 5 | 0 | 0 | 5 | 0 | 0 |
| Sorghum | 5 | 0 | 0 | 5 | 0 | 0 | 5 | 0 | 0 | 4 | 0 | 9 |
| Wild Mustard | 5 | 0 | 0 | 5 | 0 | 0 | 4 | 0 | 9 | 3 | 80 | 9 |
| Johnsongrass | 5 | 0 | 0 | 5 | 0 | 0 | 5 | 0 | 0 | 5 | 0 | 0 |
| Cocklebur | 5 | 0 | 0 | 5 | 0 | 0 | 5 | 0 | 0 | 5 | 0 | 0 |
| Morningglory | 5 | 0 | 0 | 5 | 0 | 0 | 5 | 0 | 0 | 4 | 0 | 9 |
| Purple Nutsedge | — | | | — | | | — | | | 4 | 0 | 0 |
| VIII | | | | | | | | | | | | |
| Lima Bean | 5 | 0 | 0 | 5 | 0 | 0 | 4 | 0 | 9 | 3 | 40 | 2 |
| Wild Oat | 4 | 0 | 9 | 4 | 30 | 9 | 3 | 90 | 9 | 4 | 95 | 9 |
| Barnyardgrass | 4 | 20 | 9 | 3 | 90 | 9 | 0 | 100 | 0 | 0 | 100 | 0 |
| Green Foxtail | 4 | 0 | 9 | 4 | 20 | 9 | 4 | 95 | 9 | 4 | 95 | 9 |
| Velvetleaf | 3 | 0 | 9 | 3 | 20 | 9 | 3 | 90 | 9 | 2 | 90 | 9 |
| Tomato | 4 | 0 | 9 | 4 | 0 | 9 | 3 | 0 | 9 | 3 | 30 | 9 |
| Field Bindweed | 4 | 0 | 9 | 4 | 0 | 9 | 3 | 0 | 9 | 3 | 50 | 9 |
| Soybean | 5 | 0 | 0 | 5 | 0 | 0 | 5 | 0 | 0 | 5 | 0 | 0 |
| Wild Mustard | 3 | 80 | 9 | 2 | 80 | 9 | 0 | 100 | 0 | 0 | 100 | 0 |
| Johnsongrass | 4 | 0 | 9 | 3 | 0 | 9 | 3 | 30 | 9 | 3 | 90 | 9 |
| Cocklebur | 4 | 0 | 9 | 4 | 0 | 9 | 3 | 40 | 9 | 2 | 60 | 9 |
| Morningglory | 4 | 0 | 9 | 3 | 0 | 9 | 3 | 0 | 9 | 3 | 60 | 9 |
| Sesbania | 5 | 0 | 0 | 4 | 0 | 9 | 4 | 0 | 9 | 4 | 10 | 2 |
| Yellow Nutsedge | 5 | 0 | 0 | 4 | 0 | 9 | 4 | 0 | 9 | 3 | 50 | 9 |

I claim:

1. A compound of the formula

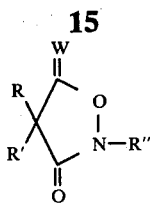

in which
R is methyl;
R' is methyl or ethyl;
W is oxygen or sulfur;
R" is —CH$_2$—Z; and
Z is phenyl substituted with fluorine, chlorine, or bromine in the 2-position, and which may be substituted with fluorine, chlorine, or bromine in the 4- or 5-position, or with methylenedioxy in the 4,5-position.

2. The compound of claim 1 in which W is oxygen.
3. The compound of claim 2 in which R' is methyl.
4. The compound of claim 3 which is 2-[(2-chlorophenyl)methyl]-4,4-dimethylisoxazolidine-3,5-dione.
5. The compound of claim 3 which is 2-[(2,4-dichlorophenyl)methyl]-4,4-dimethylisoxazolidine-3,5-dione.
6. The compound of claim 3 which is 2-[(2,5-dichlorophenyl)methyl]-4,4-dimethylisoxazolidine-3,5-dione.
7. The compound of claim 3 which is 2-[(2-fluorophenyl)methyl]-4,4-dimethylisoxazolidine-3,5-dione.
8. The compound of claim 3 which is 2-[(2-bromophenyl)methyl]-4,4-dimethylisoxazolidine-3,5-dione.
9. The compound of claim 3 which is 2-[(6-chloro-1,3-benzodioxol-5-yl)methyl]-4,4-dimethylisoxazolidine-3,5-dione.
10. The compound of claim 2 in which R' is ethyl.
11. The compound of claim 10 which is 2-[(2-chlorophenyl)methyl]-4-ethyl-4-methylisoxazolidine-3,5-dione.
12. The compound of claim 1 in which W is sulfur.
13. The compound of claim 12 which is 2-[(2-chlorophenyl)methyl]-4,4-dimethylisoxazolidine-3-one-5-thione.
14. An herbicidal composition comprising an herbicidally effective amount of a compound of claim 1 in admixture with an agriculturally acceptable carrier and a surface active agent.
15. A method of controlling undesired plant growth which comprises applying to the locus to be protected an herbicidally effective amount of a compound of claim 1.
16. The method of claim 15 in which the compound is the compound of claim 3.
17. The method of claim 16 in which the compound is the compound of claim 4.
18. The method of claim 15 in which the locus to be protected is planted with soybeans.
19. The method of claim 15 in which the locus to be protected is planted with sorghum.
20. The method of claim 15 in which the locus to be protected is planted with peanuts.
21. The method of claim 15 in which the locus to be protected is planted with lima beans.

* * * * *